United States Patent [19]

Sondahl et al.

[11] Patent Number: 5,530,182
[45] Date of Patent: Jun. 25, 1996

[54] METHODS FOR PRODUCTION F HYBRID ROSE PLANTLETS FROM ROSE SOMATIC EMBRYOS

[75] Inventors: Maro R. Sondahl; Clemencia Noriega, both of Mt. Laurel, N.J.

[73] Assignee: Florigene B.V. Europe, Rijnsburg, Netherlands

[21] Appl. No.: 352,970

[22] Filed: Dec. 9, 1994

Related U.S. Application Data

[63] Continuation of Ser. No. 150,563, Nov. 10, 1993, abandoned, which is a continuation of Ser. No. 939,546, Aug. 31, 1992, abandoned, which is a continuation of Ser. No. 542,841, Jun. 25, 1990, abandoned.

[51] Int. Cl.$^6$ ..................................................... A01H 4/00
[52] U.S. Cl. .................................. 800/200; 800/DIG. 36; 435/240.49
[58] Field of Search .......................... 435/240.4, 240.45, 435/240.49; 800/200, DIG. 30–37

[56] References Cited

U.S. PATENT DOCUMENTS 4,672,035  6/1987  Davidonis et al. ................... 455/240.4

FOREIGN PATENT DOCUMENTS 1241334  8/1960  France ................................. 800/200
1423068  1/1966  France ................................. 800/200

OTHER PUBLICATIONS

Khatamian, H., et al. "Embryogenesis and organogenesis in leaf callus of Rosa," Abstracts Viith Intl. Congress on Plant Tissue and Cell Culture. Amsterdam, Jun. 24–29, 1990, p. 256. (Abstract B4–63).
Rout, G. R. et al. "Induction of somatic embryogenesis in Rosa hybrida cv. Landora," Orissa Journal of Horticulture, vol. 17, No. 1–2, pp. 46–49, 1989.
Matthews, D., et al. "Agrobacterium–mediated genetic transformation of Rosa spp.[1]," Abstracts Viith Intl. Congress on Plant Tissue and Cell Culture, Amsterdam, Jun. 24–29, 1990, p. 69. (Abstract A2–99).
Noriega, C., et al. "Studies on plant regeneration in hybrid tea roses[1]," Abstracts Viith Intl. Congress on Plant Tissue and Cell Culture, Amsterdam, Jun. 24–29, 1990, p. 133. (Abstract A3–203).
Burger et al., 1990, Plant Cell, Tissue and Organ Culture 21:147–152.
Lloyd et al., 1988, Euphytica 37:31–36.
Khosh–Khui and Sink, 1982, Scientia Horticulturae 17:361–370.
Khosh–Kui and Sink, 1982, J. Hortic. Sci. 57:315–319.
Tabaeezadeh and Khosh–Khui, 1981, Scientia Horticulturae 15:61–66.
Hasegawa, 1979, HortScience 14:610–612.
Skirvin and chu, 1979, HortScience 14:608–610.
Nash and Davies, 1972, J. Exp. Bot. 23:75–91.
Jacobs et al., 1970, Agroplantae 2:45–49.
Jacobs et al., 1970, Agroplantae 2:25–27.
Jacobs et al., 1969, Agroplantae 1:179–188.
Jacobs et al., 1968, S. Afr. J. Agric. Sci. 11:673–678.
Hill, 1967, Nature, Nature (London) 216:596–597.
de Wit et al (1990) Plant Cell Reports 9:456–458.
Ammurato in *Handbook of Plant Cell Culture,* vol. 1 (Evans, et al, eds.) MacMillan, NY, 1983, pp. 82–123.
Zimmerman in *Cell culture and Somatic Cell Genetics of Plants,* vol. 3, (Vasil, ed.) Academic Press, Orlando, 1986, pp. 245–246 and 252.
Brown et al in *Cell culture and Somatic Cell genetics of plants,* vol. 3 (Vasil, ed), Academic Press, Orlando, 1986, pp. 49–50.
Wang et al (1984) Hort Science 19(1):71–72.
Burger et al (1990) Plant Cell, Tissue and Organ Culture 21:147–152.
Valles, et al (1987) Acta Horticulturae 212:691–696.

*Primary Examiner*—Che S. Chereskin
*Attorney, Agent, or Firm*—Townsend and Townsend and Crew

[57] ABSTRACT

The invention is directed to methods for producing somatic embryos of *Rosa hybrida* and obtaining regenerated plantlets therefrom. Somatic embryos may be produced by culturing mature tissue from *Rosa hybrida* in callus induction medium to induce callus formation and subsequently culturing the induced callus in regeneration medium which is capable of inducing completion of the development of somatic embryos. The availability of somatic embryos and the regenerative capacity of such embryos provides convenient raw material for carrying out current methods of plant transformation, such as ballistic methods of DNA delivery, or Agrobacterium culture.

68 Claims, 11 Drawing Sheets

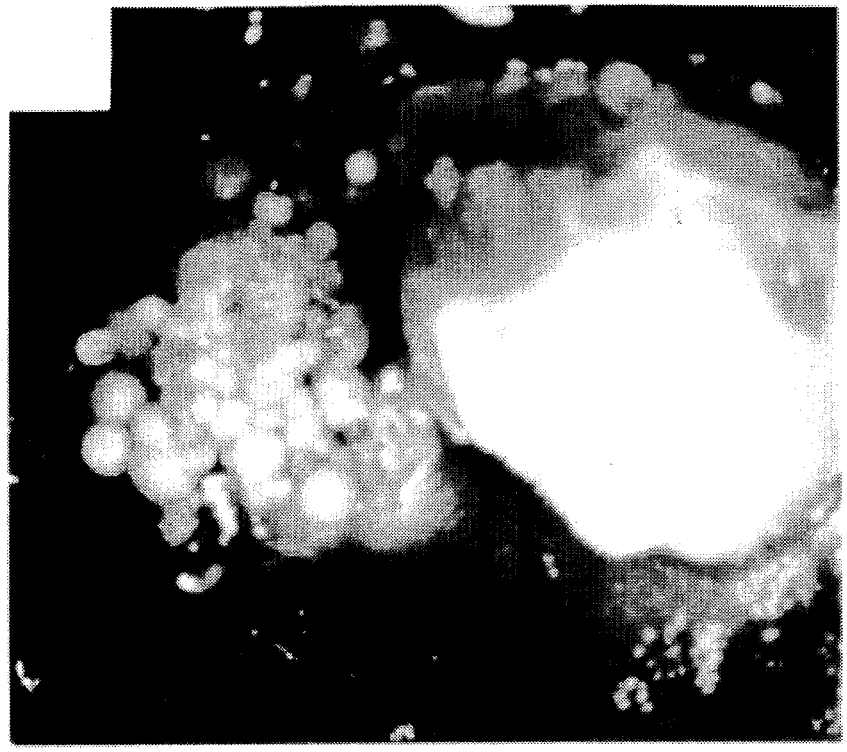
FIG. IA.
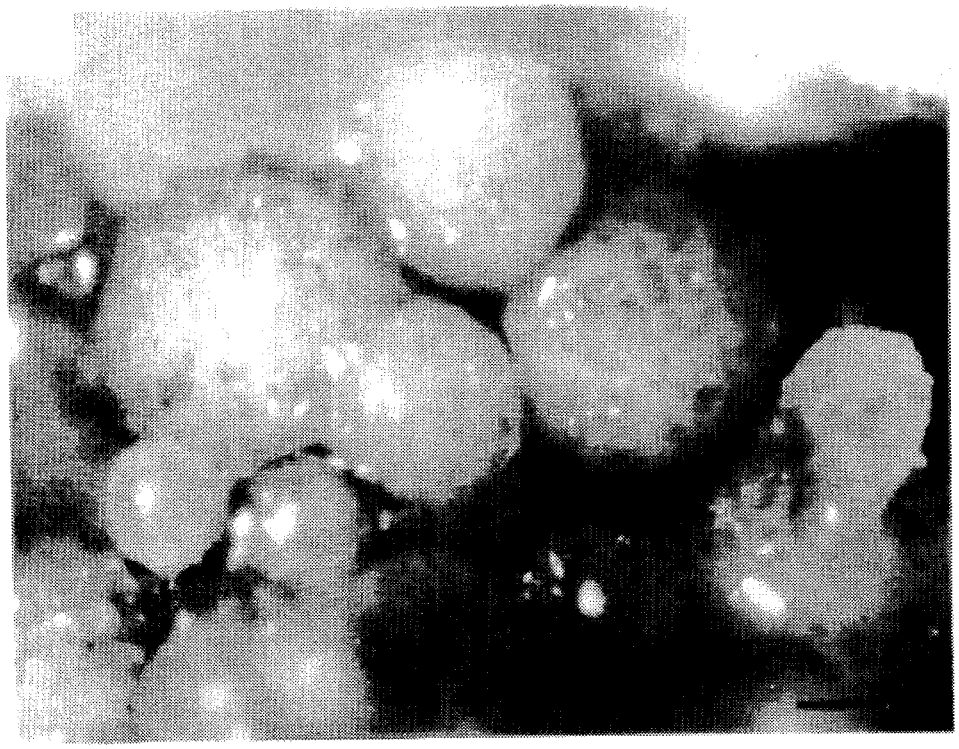
FIG. IB.

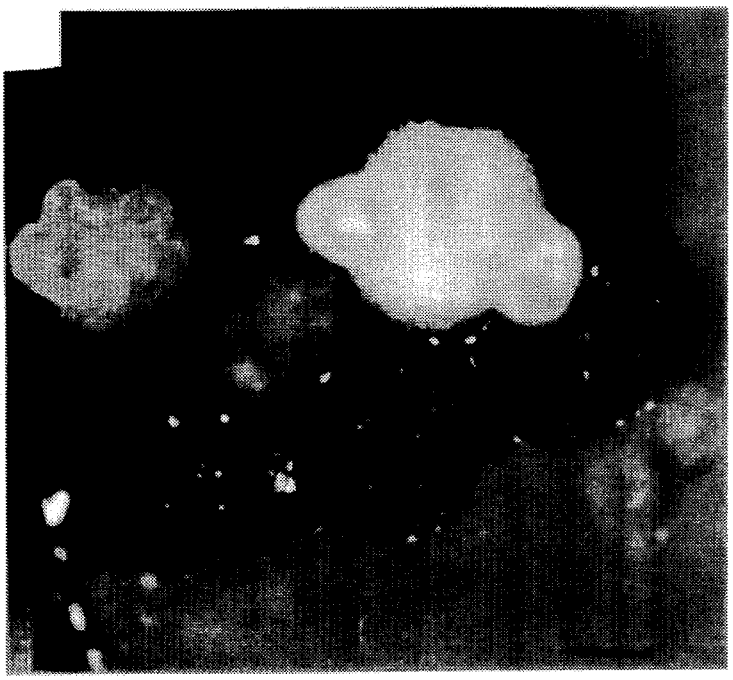
FIG. IC.
FIG. ID.
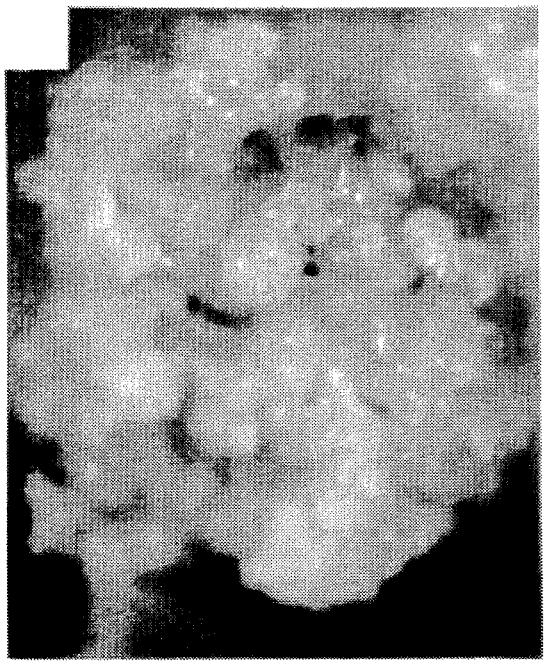
FIG. IE.
FIG. IF.

SOMATIC EMBRYOGENESIS FROM CALLUS CULTURES OF STAMEN FILAMENTS OF HYBRID TEA ROSE VAR. ROYALTY

SOMATIC EMBRYOGENESIS FROM CALLUS CULTURES OF STAMEN FILAMENTS OF HYBRID TEA ROSE VAR. ROYALTY

SOMATIC EMBRYOGENESIS FROM LEAF EXPLANTS OF HYBRID TEA ROSE VAR. SONIA

FIG. 6.

EMBRYOGENIC CELL SUSPENSION FROM MATURE
LEAF CALLUS OF HYBRID TEA ROSE VAR. ROYALTY

| TIME | MEDIUM | |
|---|---|---|
| | | MATURE LEAVES |
| | M130-7 | |
| 6W | | PRIMARY CALLUS |
| | M130-7 | |
| 3W | | OXIDIZED PRIMARY TISSUE |
| | M11 | |
| 10W | | OXIDIZED GLOBULAR STRUCTURES |
| | W25-3 | |
| 4W | | OXIDIZED GLOBULAR STRUCTURES |
| | SM-1 | |
| 3W | | FINE CELL SUSPENSION |
| | SM-1 | |
| 2W | | FINE CELL SUSPENSION |
| | W26-1 | |
| 4W | | ADVANCED EMBRYOGENIC TISSUE (GLOBULAR EMBRYOS) |

METHODS FOR PRODUCTION F HYBRID ROSE PLANTLETS FROM ROSE SOMATIC EMBRYOS

This is a continuation of Ser. No. 08/150,563, filed Nov. 10, 1993, now abandoned, which is a continuation of Ser. No. 07/939,546, filed Aug. 31, 1992, now abandoned, which is a continuation of Ser. No. 07/542,841, filed Jun. 25, 1990, now abandoned.

TABLE OF CONTENTS
1. Field of the Invention
2. Background of the Invention
3. Summary of the Invention
    3.1. Definitions
4. Brief Description of the Figures
5. Detailed Description of the Invention
    5.1. Somatic Embryo Production
        5.1.1. Callus Induction
        5.1.2. Intermediate Stages
        5.1.3. Regeneration Medium
    5.2. Maturation
    5.3. Germination
    5.4. Plantlet Production
6. Examples
    6.1. Filament Culture
    6.2. Leaf Explant
    6.3. Cell Suspension Culture

FIELD OF THE INVENTION

The present invention relates to plant tissue culture methods. More specifically, the invention relates to methods for producing somatic embryos of *Rosa hybrida*, and obtaining regenerated plants therefrom.

BACKGROUND OF THE INVENTION

The hybrid tea rose, *Rosa hybrida*, is one of the most popular of cultivated plants. As with any valuable plant species, breeders are always working to improve the existing varieties; among the characteristics in which breeders of cut flowers are interested are color, morphology, fragrancy and length of vase life of the cut flower. Despite active efforts however, improvement in roses is slow and difficult to achieve through traditional breeding methods because of its perennial nature and a high degree of sterility caused by abnormal chromosome numbers. Tissue culture often provides a natural source of variation, as well as a convenient medium in which mutagenesis can be carried out. Moreover, in vitro transformation can be used as a tool for plant improvement, provided regeneration of the transformed plants can be achieved.

Notwithstanding the desirability of having reliable tissue culture methods for rose regeneration, there has been no success in regeneration of hybrid tea roses through the somatic embryogenesis process from tissue explants or single cells in liquid culture. The earliest rose tissue cultures were based on seed embryo cultures, in which the outer coat of a seed is removed, and the water-impermeable inner seed coat penetrated with a needle to permit seed germination in vitro of the sexual embryo germination medium (Asen and Larsen, *Penn. State Col. Prog. Rep.*, No. 4, 1951). The utility of this technique is that it allows the rescue of hybrid roses which might otherwise abort, and also increases the speed of germination in rose breeding programs.

More recently callus cultures have also been established by a number of laboratories. Both Jacobs et al. (*S. Afr. J. Agric. Sci.* 11: 673–678, 1968; *Agroplantae* 1: 179–182, 1969; *Agroplantae* 2: 25–28, 1970; *Agroplantae* 2: 45–50, 1970) and Wulster and Sacalis (*Hort. Sci* 15: 736— 736, 1980) have studied the effects of growth regulators on callus. Khosh-Khui and Sink (*Sci. Hortic* 17: 361–370, 1982) have also determined a number of parameters which aid in the establishment of rose callus cultures. However, none of the cultures reported by any of these authors went further than the callus stage. Shoot primordia have been reported in long term rose callus cultures (Hill, *Nature* 216: 596–597, 1967), but no plants were ever developed from these primordia. The most recent success with rose tissue culture has been the report on organogenesis from culture of immature seed embryos (Burger et al., *Plant Cell. Tissue and Organ Culture* 21:147, 1990).

Suspension cultures from rose tissue have also reportedly been successfully established by several different laboratories (Tulecke and Nickell, *Science* 130: 863–864, 1959; Gamborg, *Exp. Cell. Res.* 50: 151–158, 1968; Nash and Davies, *J. Exp. Bot.* 23: 75–91, 1972). However, no capacity for plant regeneration has been observed in any of these cultures. These rose cell suspension lines have been used extensively for biochemical studies of in vitro plant cells.

A number of workers have also reported adventitious shoot formation from callus cultures and tissue explants. For example, Lloyd et al. (*Euphytica* 37: 31–36, 1988) describe the formation of shoots from callus of *R. persica* x *xanthina*, in the presence of 6-benzyl adenine (6-BA) and naphthalene acetic acid (NAA); however, no success was observed with *Rosa hybrida*. Axillary shoot development has also been noted by many authors as a means of rose micropropagation (Hasegawa, *Hort. Sci.* 14: 610–612, 1979; Kirvin and Chu, *Hort. Sci.* 14: 608–610, 1979; Khosh-Khui and Sink, *J. Hortic. Sci.* 57: 315–319, 1982).

As can be seen from the foregoing review, although there has been some success in rose tissue culture there has not yet been a successful effort in regenerating an entire rose plant from *Rosa hybrida* through a somatic embryogenesis process. The recovery of plants from the meristematic tissues of axillary buds is not a regeneration process but rather the development of pre-existing meristems. There is thus still a need for a reliable method of regeneration from nonmeristematic tissue, which will provide the flexibility needed for successful practice of plant manipulation techniques, e.g. in vitro genetic manipulation. In vitro genetic manipulation will include protoplast fusion and gene uptake among others.

SUMMARY OF THE INVENTION

The invention is directed to a method for controlled regeneration of a *Rosa hybrida* plantlet from a somatic embryo which comprises:

(a) providing a somatic embryo;

(b) culturing the somatic embryo on a maturation medium capable of inducing differentiation of the embryo to yield a differentiated embryo;

(c) germinating the differentiated embryo on germination medium to yield a germinated embryo; and (d) propagating the germinated embryo on propagation medium to produce a mature plantlet capable of being transferred to soil conditions.

The invention is further directed to a method for obtaining at least one somatic embryo from mature somatic tissue of *Rosa hybrida* which comprises:

(a) culturing mature somatic tissue on callus induction medium comprising effective amounts of a nutrient medium, an energy source, an auxin and a cytokinin to obtain at least one induced callus; and (b) culturing the induced callus in a regeneration media capable of inducing completion of the development of somatic embryos comprising effective amounts of a nutrient medium, an energy source, an auxin and a cytokinin to obtain at least one somatic embryo.

The mature somatic tissue may for example be obtained from a stamen filament, a leaf explant or a cell suspension culture. If the mature somatic tissue is obtained from a stamen filament or cell suspension culture, the ratio of auxin to cytokinin in the regeneration medium may be decreased by a factor of at least two to about 15 relative to the ratio of auxin to cytokinin present in callus induction medium and/or the source of the auxin and cytokinin in the regeneration differs from the source of the auxin and cytokinin in the callus induction medium. In other words, the ratio of auxin to cytokinin in the regeneration medium may be two to fifteen fold less than the ratio of auxin to cytokinin in the induction medium if the somatic tissue is obtained from a stamen filament or cell suspension culture. If the mature somatic tissue is obtained from a leaf explant, the ratio of auxin to cytokinin may be increased relative to the ratio of auxin to cytokinin present in callus induction medium and/or the source of the auxin and cytokinin in the regeneration differs from the source of the auxin and cytokinin in the callus induction medium.

The availability of somatic embryos, and the developmental capacity of such embryos provides convenient raw material for carrying out current methods of plant transformation, such as ballistic methods of DNA delivery, or Agrobacterium culture.

DEFINITIONS

"Nutrient media" as used herein refers to media that comprises salts, a carbon source and vitamins at concentrations necessary to effect the maintenance of cultured plant cells "Effective amounts" as used herein refers to the amount of a given component necessary to effect the recited step.

As used throughout the present specification and claims, "somatic embryo" is intended to mean an embryo (or embryoid) which is initiated from a somatic cell or cells and is distinguished from a zygotic embryo, which is formed in a seed, from a fertilized egg. The plants derived from the rose somatic embryos are distinguished from previous tissue culture-produced rose plants in that the plants are not obtained simply by stimulation of growth of preformed meristematic tissue.

As used herein, "rose", unless otherwise specified, refers to the modern rose, also known as the hybrid tea rose or Rosa hybrida.

BRIEF DESCRIPTION OF THE FIGURES

FIG. 6 shows the general procedure used to generate somatic embryos from cell suspensions from Rosa hybrida var. Royalty.

DETAILED DESCRIPTION OF THE INVENTION

Figure 1G:
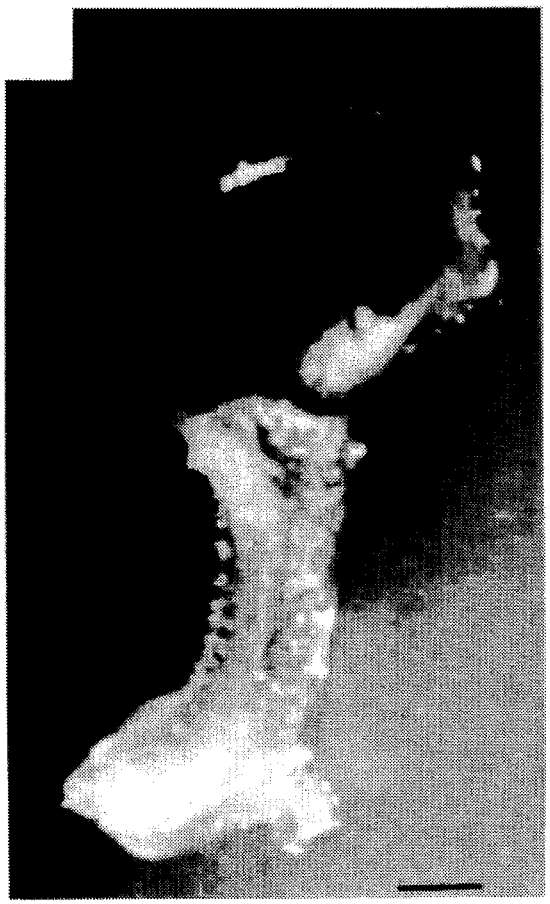
FIG. 1 shows various stages of somatic embryogenesis from filament explants of Rosa hybrida var. Royalty. (A) Early stage of differentiation from primary callus (right) and globular embryos (left); bar 2.0 mm; (B) Globular embryo proliferation; note the presence of multiple buddings from pre-existing embryos; bar 0.7 mm; (C) Cotyledonary leaf formation during early stages of embryo development; bar 0.8 mm; (D) Cotyledonary leaf differentiation; bar 1.0 mm; (E) Friable embryogenic tissue derived from somatic embryos; bar 1.0 mm; (F) Multiple somatic embryos at late stages of development; bar 1.7 mm; (G) Early stage of embryo germination characterized by hypocotyl elongation and cotyledonary leaf expansion; bar 1.2 mm; (H) Germinated somatic embryo of rose after 3 weeks in germination medium; bar 1.2 mm.
Figure 1H:

The invention is directed to methods producing at least one somatic embryo of Rosa hybrida, and obtaining at least one regenerated plant therefrom. Four steps are involved in obtaining mature plantlets using the method of the present invention: (a) production of a somatic embryo; (b) culturing the somatic embryo on a maturation medium capable of inducing differentiation of the embryo; (c) germinating the differentiated embryo on germination medium; and (d) propagating the germinated embryo on propagation medium to produce a mature plantlet capable of being transferred to soil conditions.

SOMATIC EMBRYO PRODUCTION

Two steps are involved in the production of a somatic embryo(s) from mature somatic tissue of Rosa hybrida: (a) culturing mature somatic tissue on callus induction medium comprising effective amounts of a nutrient medium, an energy source, an auxin and a cytokinin to obtain at least one induced callus; and (b) culturing the induced callus or calli in a regeneration media capable of inducing completion of the development of somatic embryos comprising effective amounts of a nutrient medium, an energy source, an auxin and a cytokinin to obtain somatic embryos. In one embodiment, a step which comprises the culturing of the induced callus or calli on maintenance media to isolate the induced callus or calli and increase the quantity of induced calli before the induced calli may be regenerated to produce somatic embryos.

CALLUS INDUCTION

Each induction medium requires a certain basal composition to maintain callus growth; the minimal elements include an appropriate nutrient media, an energy source, and the appropriate growth regulators. A variety of nutrient media are known which provide adequate supplies of nitrogen and salts to support callus growth; among these are White's, B5, N6 and MS medium. Callus morphology may be hard, spongy, watery, sandy, globular, or have a white, cream or yellow color depending on the type of medium used.

Any sugar may be employed as energy source. Among the appropriate choices are glucose, maltose, sucrose, or lactose, or sucrose in combination with any of the named sugars, or mannose. A preferred sugar for this purpose is sucrose, at a level of about 10–50 g/l, but molar equivalents of other sugars may also be employed.

Callus induction medium preferably contains at least one auxin and at least one cytokinin. The auxins may be any auxin, natural or synthetic, for example, indole acetic acid (IAA), naphthalene acetic acid (NAA), (2,4-dichlorophenoxy) acetic acid (2,4-D) and picloram. Cytokinin may be selected from any of the known cytokinin, natural or synthetic, for example 6-benzyladenine (6-BA), zeatin (ZEA), kinetin (KIN), and isopentyladenosine (iP). Callus will be induced in the presence of several combinations of auxin and cytokinin. However, superior results are observed on an induction medium comprising 2,4D and zeatin. An alternate useful combination is NAA with kinetin. Generally, an auxin will be present in an amount of about 0.1–10 mg/l, and cytokinin in an amount of 0.2–15.0 mg/l. When the auxin is NAA, the concentration in the medium is preferably from about 0.5–2.5 mg/l, and most preferably about 2.0 mg/l. When 2,4-D is used, the amount is preferably from about 0.5–10.0 mg/l and most preferably about 2.5 mg/l. When the cytokinin is kinetin, the concentration in the medium is preferably from about 0.5–5.0 mg/l and most preferably about 0.5 mg/l. When zeatin is used, the concentration is preferably from about 0.2–12.5 mg/l and most preferably about 1.5 mg/l. Other nonessential components may also be added to the medium to optimize callus induction. For example, amino acids, such as glycine, may be employed as a nitrogen source. In certain embodiments, use of additional growth regulators may be helpful in promoting callus induction. For example, addition of abscisic acid (ABA), in the amount of about 0.1–0.2 mg/l may be useful in callus induction, particularly to promote a more globular callus, which leads to embryogenic tissue. ABA may be used with all explant sources, but has been especially useful with the culture of in vitro leaf explants.

Those skilled in the art will recognize other components which are frequently employed in plant tissue culture. Addition of various vitamins, e.g. MS vitamins, White vitamins, nicotinic acid, inositol, pyridoxine or thiamine is common. Similarly, for solid media, an appropriate amount of solidifying agent is also added to the mixture. The tissue may be cultured in induction medium for 3–9 weeks.

INTERMEDIATE STAGES

Prior to transfer of callus to regeneration medium, it may be desirable to transfer the callus to a maintenance medium. This medium is used to isolate preembryogenic callus, and to favor this type of callus prior to regeneration. Although regeneration can occur without a maturation phase, the transfer of callus to a maintenance medium permits better control and proliferation of a particular callus cell line.

The primary components of a maintenance medium are, an appropriate basic medium with inorganic nutrients, at least one growth regulator, and energy sources. As in Section 5.1., supra, any sugar may be used as an energy source. The growth regulator may be selected from the group including but not limited to an auxin, a cytokinin, abscisic acid, and gibberellic acid. The auxins may be any auxin, natural or synthetic, for example, IAA, NAA, 2,4-D, and picloram. An auxin will be present in an amount of about 0.1–10 mg/l. Cytokinin may be selected from any of the known cytokinin, natural or synthetic, for example, 6-BA, ZEA, KIN, and iP. A cytokinin may be present in an amount of about 0.2–15.0 mg/l. Abscisic acid may be present in the amount of about 0.2–2 mg/l. Gibberellic acid may be present in the amount of about 0.5–5 mg/l.

Callus maintenance is continued for as long as practically possible, preferably with periodic subculturing. Generally, preembryogenic callus can be maintained for about 12–24 months.

In a specific embodiment, where embryos are generated from a cell suspension, the cells after induction, may be transferred to a specific maintenance medium, SM-1, medium which promotes cell proliferation without oxidation of tissue explants in culture. The utility of the SM-1 medium lies in the presence of ABA, and 2,4-D. In a preferred embodiment, 2,4-D is present at a concentration of about 1.65 mg/l and ABA is present at a concentration of about 0.26 mg/l. Following culture in SM-1, the tissue becomes white and compact and eventually begins to form small cell clumps which provide the basis for the fine cell suspensions necessary for successful completion of the method.

Additionally, in the specific case of cell suspension cultures, one or more conditioning media may be used prior to transfer to maintenance media to enable the selection of a friable cell line in liquid culture. The conditioning media comprises an appropriate basic medium with inorganic nutrients, a growth regulator, and an energy source. As in Section 5.1.1., supra, any sugar may be used as an energy source. The growth regulator may selected from the group including but not limited to an auxin, a cytokinin, abscisic acid, and gibberellic acid. The auxins may be any auxin, natural or synthetic, for example, IAA, NAA, 2,4-D, and picloram. An auxin will be present in an amount of about 0.1–10 mg/l. Cytokinin may be selected from any of the known cytokinin, natural or synthetic, for example, 6-BA, ZEA, KIN, and iP. A cytokinin may be present in an amount of about 0.2–15.0 mg/l. Abscisic acid may be present in the amount of about 0.2–2 mg/l. Gibberellic acid may be present in the amount of about 0.5–5 mg/l. The callus may be cultured in the conditioning media for about 3–6 weeks.

REGENERATION MEDIUM

Following culture on induction and optionally maintenance media, the calli are transferred to a new medium for regeneration of somatic embryos. This medium contains as its principal elements an auxin, a cytokinin, an energy source, named in Section 5.1.1, supra and an appropriate nutrient medium selected from the group consisting of White's and B5 media.

The mature somatic tissue may as stated in Section 5.1.1. supra, for example be obtained from a stamen filament, a leaf explant or a cell suspension culture. If the mature somatic tissue is obtained from a stamen filament or cell suspension culture, the ratio of auxin to cytokinin may be decreased by a factor of at least two and up to as much as 15 relative to the ratio of auxin to cytokinin present in callus induction medium and/or the source of the auxin and cytokinin in the regeneration differs from the source of the auxin and cytokinin in the callus induction medium. In a preferred embodiment, a weaker cytokinin and auxin is used in the regeneration media than in the induction media. Specifically, 2,4-D is a stronger auxin, i.e. has a greater effect on growth regulation than NAA and zeatin is a stronger cytokinin than kinetin. As an example, regeneration of filaments can occur in a medium comprising 2,4-D/zeatin at a ratio of 1.3, compared with NAA/kinetin at a ratio of 4.0 in callus induction medium.

If the mature somatic tissue is obtained from a leaf explant, the ratio of auxin to cytokinin may be increased relative to the ratio of auxin to cytokinin present in callus induction medium and/or the source of the auxin and cytokinin in the regeneration medium differs from the source of the auxin and cytokinin in the callus induction medium. As an example, regeneration of leaf explants can occur in a medium comprising NAA/KIN at a ratio of 2.0 compared with 2,4-D/zeatin at a ratio of 1.3.

The period for regeneration generally takes about 3–6 weeks. Globular embryos will be apparent on the surface of the culture at this time (See FIGS. 1A, 2C, 2D, 3D). In many cases, the embryos so formed are capable, upon such culture, to give rise on their outer surface to secondary embryos. If this secondary embryo production is specifically desired, the globular embryos can be transferred to fresh regeneration media and cultured from 3 to 6 weeks.

EMBRYO MATURATION

The embryos produced by the method described above can be repeatedly subcultured in order to provide a larger number of embryos. These embryos are also useful targets for plant transformation via ballistic methods (Sanford, etc.). Production of mature plants from the somatic embryos is always desirable. Maturation of somatic embryos is accomplished by transfer of globular embryos to a medium comprising preferably N6 or MS nutrient media an energy source, e.g. sugar (see Section 5.1. supra for examples of sugars that may be used) and a growth regulator which may include but is not limited to an auxin, a cytokinin, abscisic acid, and gibberellic acid. The auxins may be any auxin, natural or synthetic, for example, IAA, NAA, 2,4-D, and picloram. An auxin will be present in an amount of about 0.1–10 mg/l. Cytokinin may be selected from any of the known cytokinin, natural or synthetic, for example, 6-BA, ZEA, KIN, and iP. A cytokinin may be present in an amount of about 0.2–15.0 mg/l. Abscisic acid may be present in the amount of about 0.2–2 mg/l. Gibberellic acid may be present in the amount of about 0.5–5 mg/l. The somatic embryos may be cultured on maturation media for about 3–14 weeks.

EMBRYO GERMINATION

The differentiated embryos are subsequently transferred to a germination media which may comprise N6 or MS nutrient media and an energy source, e.g. sugar (see Section 5.1.1. supra for examples of sugars that may be used). The media may further comprise a growth regulator which may include but is not limited to a cytokinin, abscisic acid, and gibberellic acid. The cytokinin may be present at a concentration of abut 0.1–1.0 mg/l. Abscisic acid may be present in the amount of about 0.2–2 mg/l. Gibberellic acid may be present in the amount of about 0.5–5 mg/l. The germination media may also further comprise coconut water at about 5–15%, v/v.

Early stages of embryo germination are characterized by hypocotyl elongation, conical cotyledonary leaves and chlorophyll development. In late stages of germination, cotyledonary leaves enlarge the hypocotyl elongates and a tap root develops. The differentiated embryos may be cultured on germination media for about 1–4 weeks.

PLANTLET PRODUCTION

The germinated embryos are subsequently propagated in propagation medium which comprises an appropriate nutrient media, an energy source, an auxin and a cytokinin. In a preferred embodiment, the auxin is IAA, present at a concentration of about 0.3 mg/l and the cytokinin is 6-BA, present at a concentration of about 3.0 mg/l. The nutrient media is selected from the group including but not limited to White's, MS, B5, and N6 media. As discussed in Section 5.1., supra, any sugar may be employed as an energy source. The auxins may be any auxin, natural or synthetic, for example, IAA, NAA, 2,4-D and picloram. An auxin will be present in an amount of about 0.1–10 mg/l. Cytokinin may be selected from any of the known cytokinin, natural or synthetic, for example, 6-BA, ZEA, KIN, and iP. A cytokinin may be present in an amount of about 0.2–15.0 mg/l.

The germinated embryos may be cultured in propagation medium for about 4–8 weeks. Well developed plantlets may be obtained and can be transferred to for example artificial soil. In one embodiment, multiple shoots can be isolated from one single plantlet before transferring to soil.

The methods described above, and in the following examples, have been applied to a number of different hybrid tea varieties, including "Sonia" and "Royalty". The success of the protocols may to some extent be genotype specific; however, the eventual success of the method with any given variety can be determined by selection of a friable pre-embryogenic tissue utilizing one of the induction media described in Section 5.1., supra. Thus, one skilled in the art can readily adapt the present method to other varieties.

The following examples illustrate the practice of the present method.

FILAMENT CULTURE

Figure 4A:
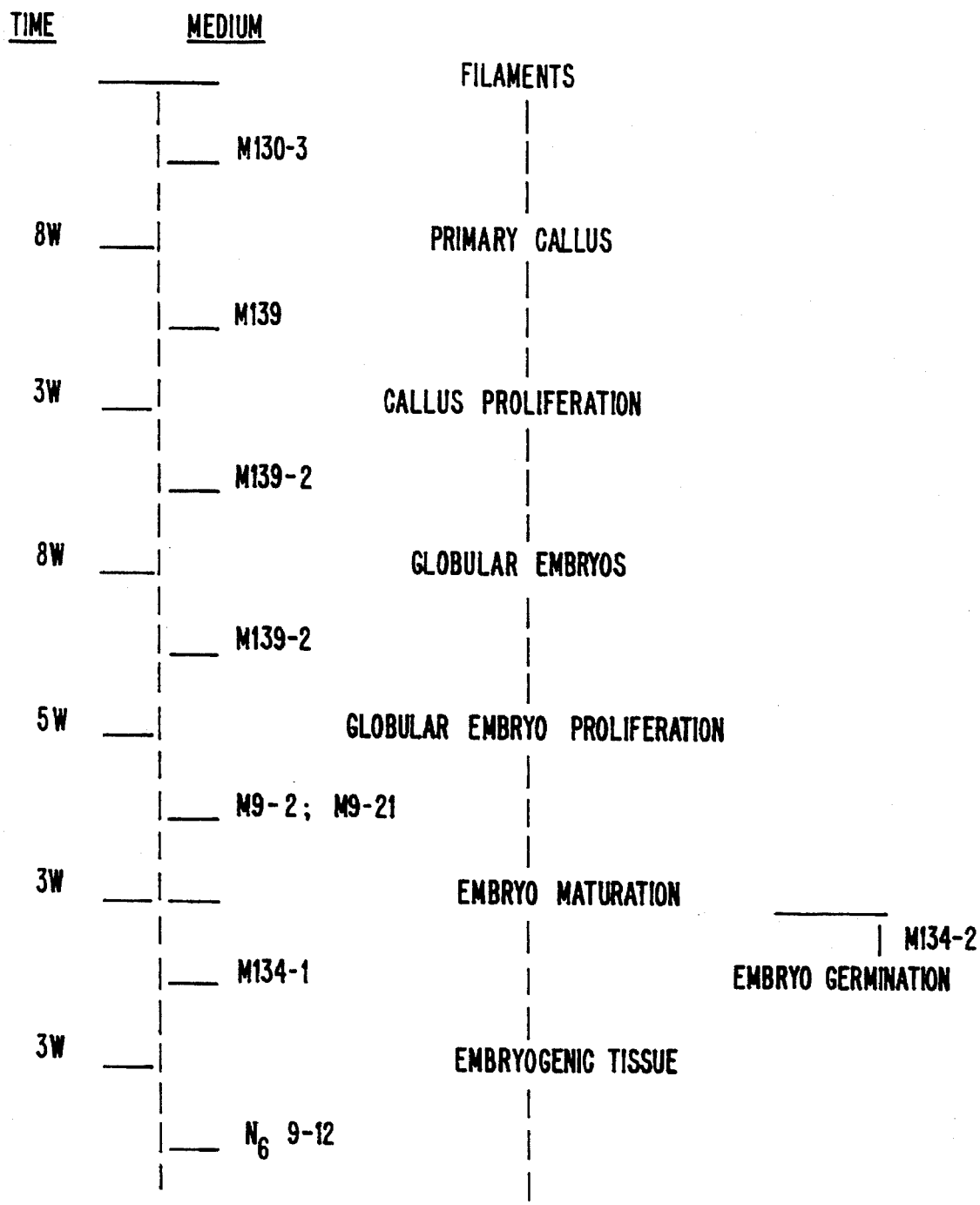
FIGS. 4A and 4B together form a chart setting forth the general procedure used to generate plantlets from stamen filaments from Rosa hybrida var. Royalty.
Figure 4B:
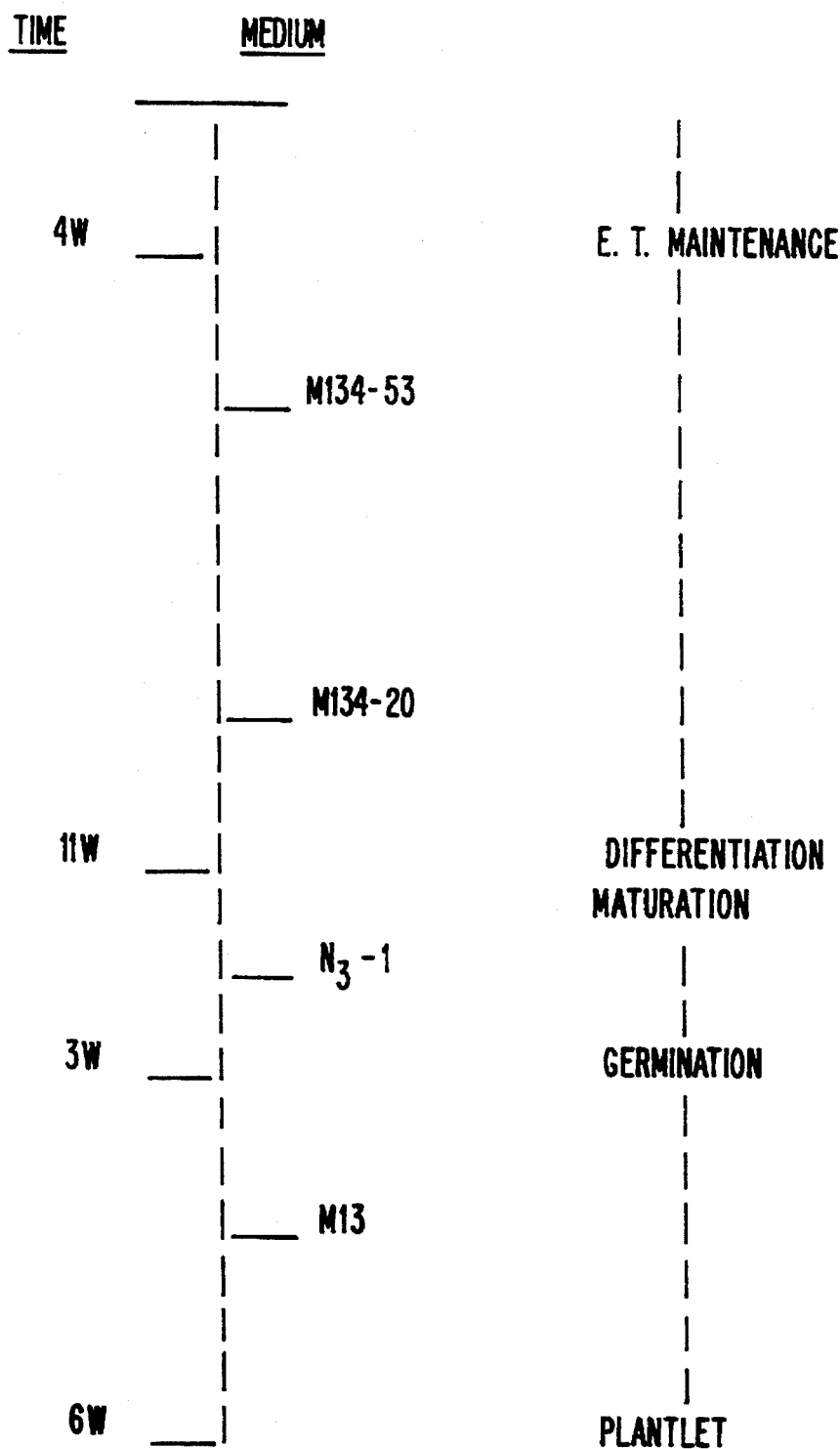

The general scheme for obtaining plantlets from filaments is shown in FIG. 4. Stamen filaments of *Rosa hybrida* L. var. Royalty were excised from flower buds of ca. 1.5 cm long, after a cold pretreatment at 2° C. during 14 days. Buds were disinfected with clorox (10%)/Tween-20 (0.1%) for 20 mins. and then rinsed three times with sterile deionized water. The callus induction medium (M130–3) consisted of MS salts (Murashige and Skoog, *Physiol. Plantae* 15:473–497 1962), MS vitamins, glycine (2 mg/l), KIN (0.5 mg/l), NAA (2 mg/l), sucrose (30 g/l), and gelrite (2.4 g/l); pH 5.7.

All media were autoclaved for 20 min. at 24° C. and 15 psi after pH adjustment. Cultures in petri dishes were sealed with Parafilm and kept in dark at 24° C.

A fast-growing, semi-hard, yellow callus was obtained from filament explants after 3 weeks in M130–3. After subculture in this medium, the callus changed to a drier appearance.

For callus maintenance, the medium M139 was used. M139 was based on B-5 salts (Gamborg et al., *Exp. Cell Res.* 50: 151–158, 1968) supplemented with ammonium sulfate 329 mg/l, thiamine-HCl (5 mg/l), inositol (100 mg/l), pyridoxine (1.5 mg/l), nicotinic acid (1.5 mg/l), glycine (2.0 mg/l), 2,4-D (1.55 m/l), sucrose (30 g/l), and gelrite (2.4 g/l); pH 5.6. M139 medium improved callus quality preventing oxidation and leading to a less compact callus.

The basic M139 medium with modified growth regulators, 2,4-D (2.0 mg/l) and zeatin (1.5 mg/l), was used as regeneration medium (M139-2). Early stages of regeneration were observed after 8 weeks of callus culture on M139-2 at a frequency of 1.43% (FIG. 1A). Globular embryos were subcultured on the same medium and secondary embryos (FIG. 1B) were formed on the outer surface of the primary embryos. The embryos matured 3 weeks after being transferred onto M9-21 and M9-2 (FIGS. 1C–D). The M9-21 medium was based on N6 salts (Chu et al., *Scientia Sinica* 18: 659–668, 1975) with 2,4-D (1 mg/l) and zeatin (0.75 mg/l); the M9-2 medium used MS salts supplemented with 2,4-D (2 mg/l) and zeatin (1.5 mg/l). Other components remained unchanged from M139, except sucrose (20 g/l).

Embryos germinated 3 weeks after being transferred to M134-2 which consisted of MS salts, thiamine-HCl (5 mg/l), inositol (100 m/l), pinidotime (1.5 mg/l), nicotinic acid (1.5 mg/l), glycine (2 mg/l), coconut water (154.), gibberellic acid 3 GA3 (1.0 mg/l), ABA (0.2 mg/l), KM-8P Vitamins, sucrose (20 g/l) and gelrite (2.4 g/l). The pH was adjusted to 5.7 before autoclaving. Great morphological variability was observed among germinating embryos varying from normal types to very short hypocotyl axis, abnormal number and shape of cotyledonary leaves, and presence or absence of roots. Most of these abnormal embryos resulted from precocious germination. Normal germination was observed from isolated embryos or embryo clusters. Early stages of germination were characterized by hypocotyl elongation and presence of conical shape cotyledonary leaves (FIGS. 1F–G). Late germinating embryos were distinguished by the opening of the concrescent cotyledonary leaves, further elongation of hypocotyl, and development of a strong tap root. The abnormal embryos proved to be an excellent source to establish new cultures with regeneration capacity upon transfer to a proliferation medium, M134-1, which was based on MS salts plus thiamine-HCl (5 mg/l), inositol (100 mg/l), pyridoxine (1.5 mg/l), nicotinic acid (1.5 mg/l), glycine (1.5 mg/l), zeatin (1.5 mg/l), NAA (0.025 mg/l), (GA3) (1.0 mg/l) sucrose (20 g/l), gelrite (2.4 g/l) pH 5.7. KM-8P vitamins (Kao and Michayluk, *Planta* 126:105–110, 1975) and growth regulators were filter sterilized and added into the autoclaved portion of this culture medium. After 3 weeks, the embryos originated a very fast-growing, friable, and white embryogenic tissue (FIG. 1E) with the presence of globular, very glossy embryos. Periodic subculture of this embryogenic tissue on the same medium maintained its capacity to proliferate and to produce globular embryos.

Tissue from the matured embryos alternatively were transferred to $N_6$9-12 medium. $N_6$9-12 medium consists of $N_6$ salts (1X), plus thiamine-HCl (5 mg/l), inositol (100 mg/l), pyridoxine (1.5 mg/l), nicotinic acid (1.5 mg/l), glycine (2 mg/l), 2,4-D (5.0 mg/l), zeatin (1.0 mg/l), (GA3) (1.0 mg/l), KAO vitamins (1X), sucrose (20 g/l), gelrite (2.4 g/l), pH 5.5. Such tissue was able to be maintained on $N_6$9-12 medium for 8 months.

The tissue was then transferred to maturation medium M134-53 for 3–5 weeks. M134-53 consists of MS salts (1X), plus thiamine-HCl (5 mg/l), inositol (100 mg/l), pyridoxine (1.5 mg/l), nicotinic acid (1.5 mg/l), glycine (2 mg/l), gibberellic acid 3 (GA3) (1.0 mg/l), ABA (2.0 mg/l), sucrose (20 g/l), gelrite (2.4 g/l) pH 5.5. The tissue was subsequently cultured in maturation medium M134-20 for 9–11 weeks. M134-53 consists of MS salts (1X), plus thiamine-HCl (5 mg/l), inositol (100 mg/l), pyridoxine (1.5 mg/l), nicotinic acid (1.5 mg/l), glycine (0.2 mg/l), (GA3) (1.0 mg/l), ABA (2.0 mg/l), KAO vitamins (1X), coconut water (10% v/v), sucrose (20 g/l), gelrite (2.4 g/l), pH 5.5.

Germination of the matured embryonic tissue was accomplished in $N_3$-1 medium. $N_3$-1 medium consists of: $N_6$ salts (½X), plus thiamine-HCl (1.0 mg/l), sucrose (20 g/l), gelrite (2.4 g/l), pH 5.6. The tissue was incubated on $N_3$-1 medium for 3 weeks.

Fully germinated embryos were transferred to M13 medium to complete plantlet development. M13 medium consists of MS salts (1X), plus thiamine-HCl (5 mg/l), inositol (100 mg/l), pyridoxine (1.5 mg/l), nicotinic acid (1.5 mg/l), glycine (0.2 mg/l), 6-BA (3.0 mg/l), IAA (0.3 mg/l), agar (6.0 g/l), sucrose (30 g/l), pH 5.8. After 6 weeks, well developed plantlets were obtained and were in condition for transfer to artificial soil. Axillary shoot proliferation was observed.

IN VITRO LEAF EXPLANT

Figure 2A:
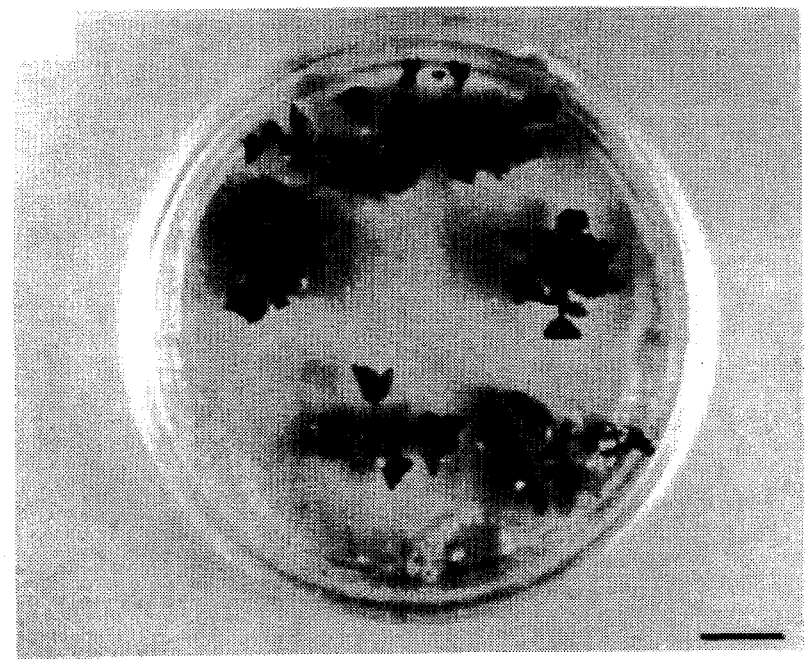
FIG. 2 shows various stages of somatic embryogenesis from leaf explants of Rosa hybrida var. Sonia. (A) Shoots from axillary buds after 3 weeks in culture; bar 14.3 mm; (B) Spongy callus formed from leaf after 4 weeks on primary medium; bar 1.1 mm; (C) Early stages of embryo differentiation from primary callus after 6 weeks on regeneration medium; bar 1.2 mm; (D) Globular embryo differentiation from semi-friable embryogenic tissue; bar 1.2 mm; (E) Globular embryo proliferation; bar 1.2 mm; (F) Enlargement of globular embryo proliferation; bar 0.5 mm.
Figure 5:
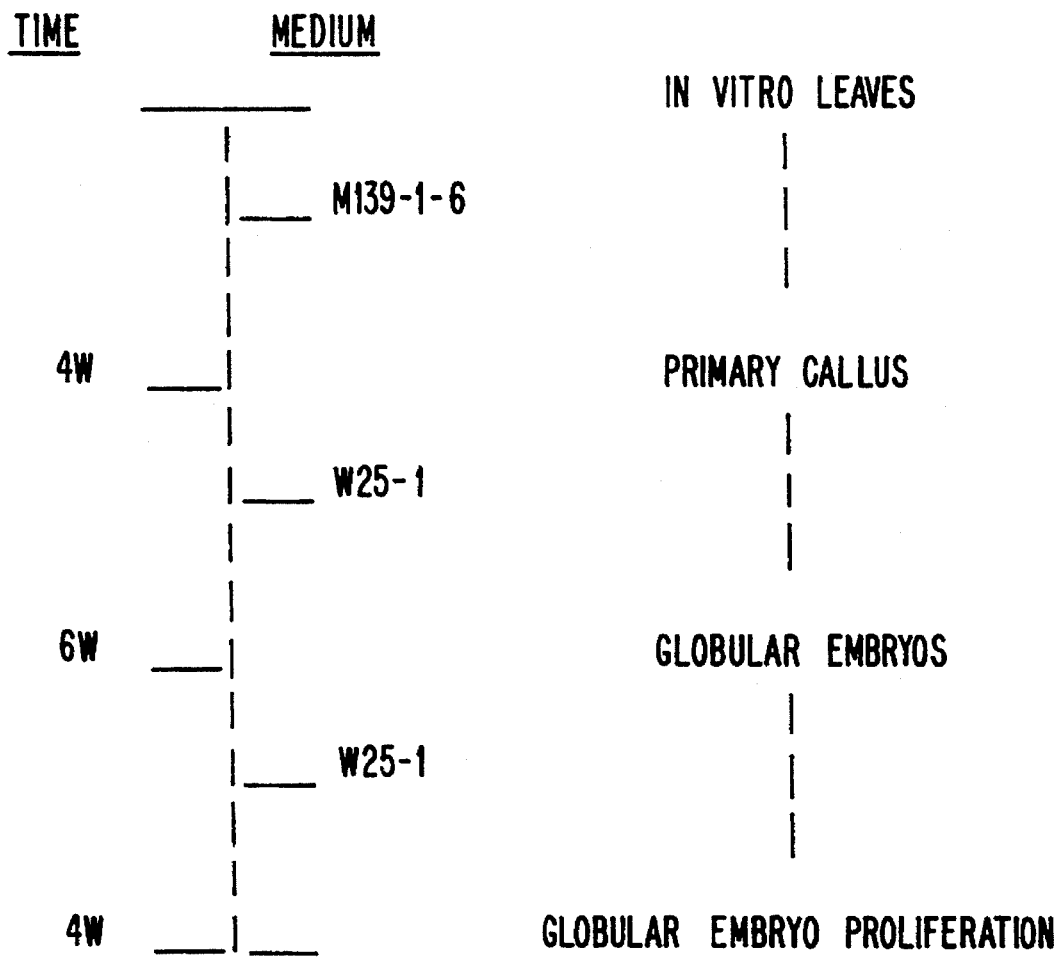
FIG. 5 shows the general procedure used to generate somatic embryos from leaf explants from Rosa hybrida var. Sonia.

Methods used to produce somatic embryos from leaf explants from *Rosa hybrida* L. var. Sonia are shown in FIG. 5. Leaves from in vitro shoots of *Rosa hybrida* L. var. Sonia (FIG. 2A) were used as explant source for callus induction. Shoots from lateral buds were cultured on Hasegawa medium (Hasegawa, *Hort. Sci.* 14:610–612, 1979). Leaf bases and apical regions were removed before inoculation.

Figure 2B:
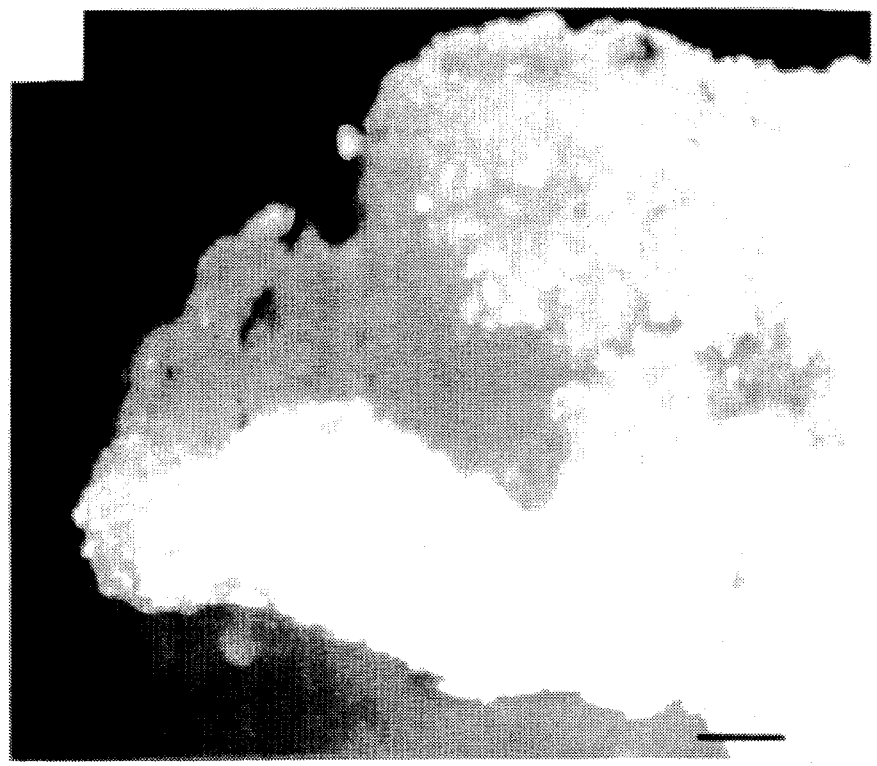
Figure 2C:
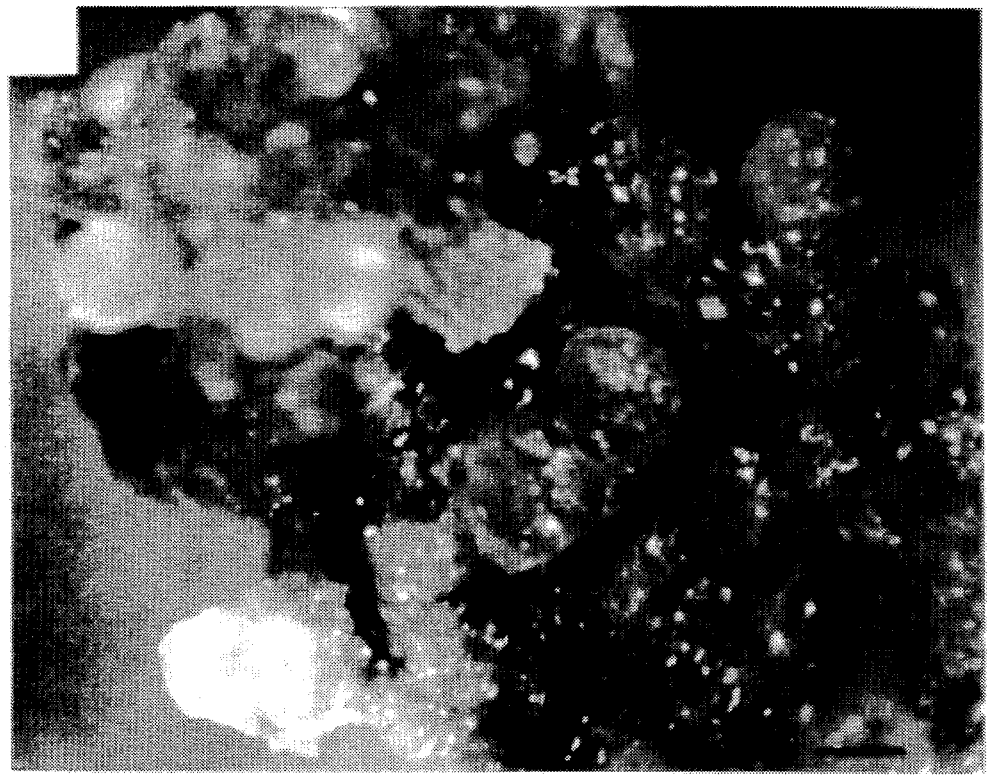
Figure 2D:
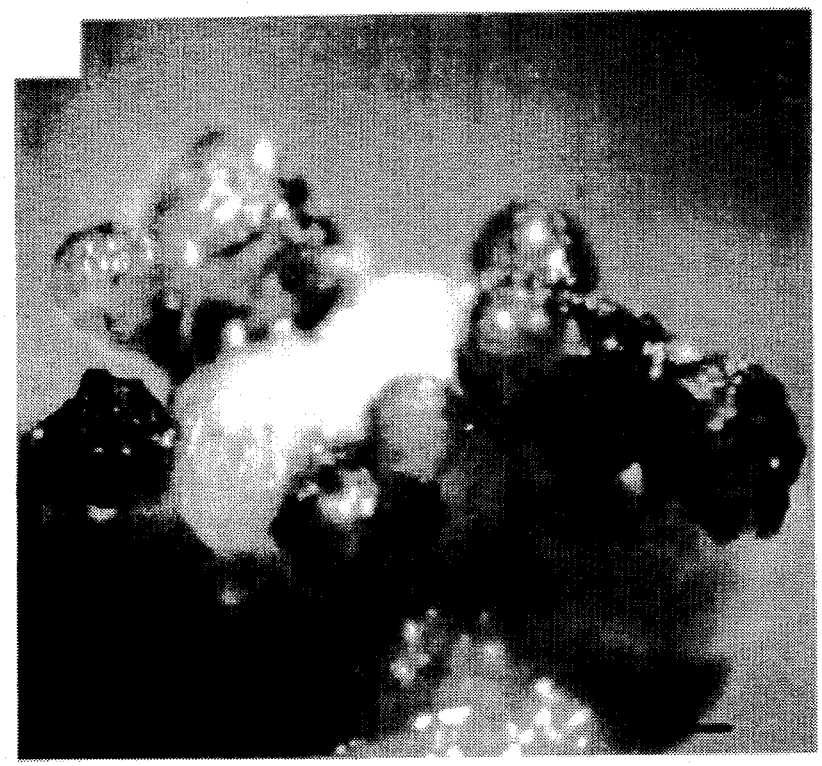
Figure 2E:
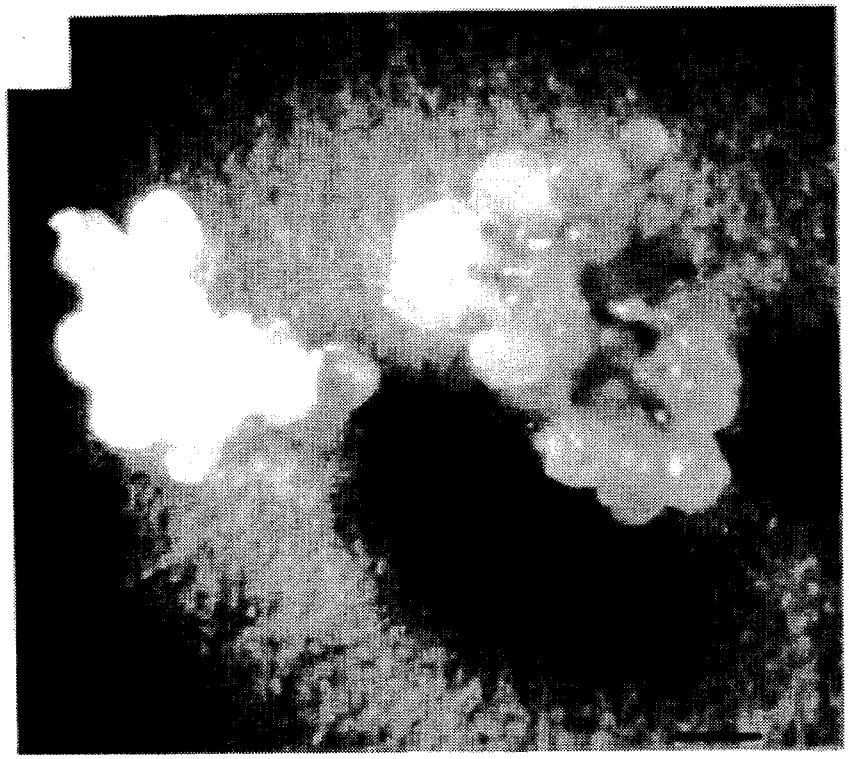
Figure 2F:
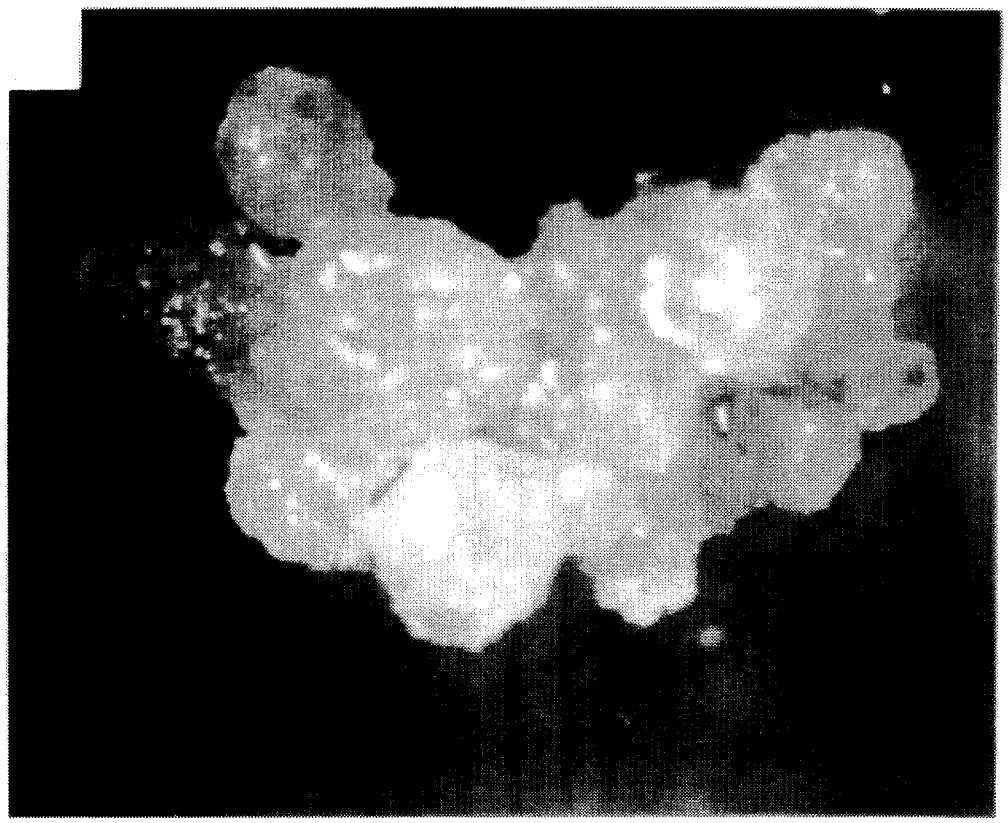

Callus induction medium was the same M139 described above with varying hormone concentrations: 2,4-D (1.5–2.0 mg/l), Zeatin (1.0–2.0 mg/l) and ABA (0–0.2 mg/l). Leaves cultured in this callus induction media formed a very spongy tissue after 3–4 weeks (FIG. 2B). These spongy calli were cultured in W25-1 consisting of White salts (White, *Handbook of Plant Tissue Culture*, Lancaster, USA 1943), with MS 0.5X iron solution, White vitamins and amino acids, KIN (2.0 mg/l), NAA (4 mg/l), GA3 (1.0 mg/l), sucrose (20 g/l), and Sigma agar (8 g/l); pH 5. Here they turned from light green amorphous callus to whitish semi-friable callus, originating free globular embryos after 4–6 weeks (FIG. 2C and D). Subculture of these globular embryos in the same medium induced secondary embryo formation (FIG. 2E). This ability to form additional secondary embryos lasted during four successive subcultures. Globular structures produced after the 4th subculture turned very hard, swollen and bumpy, giving origin later to a very dry callus.

CELL SUSPENSION CULTURE

Figure 3A:
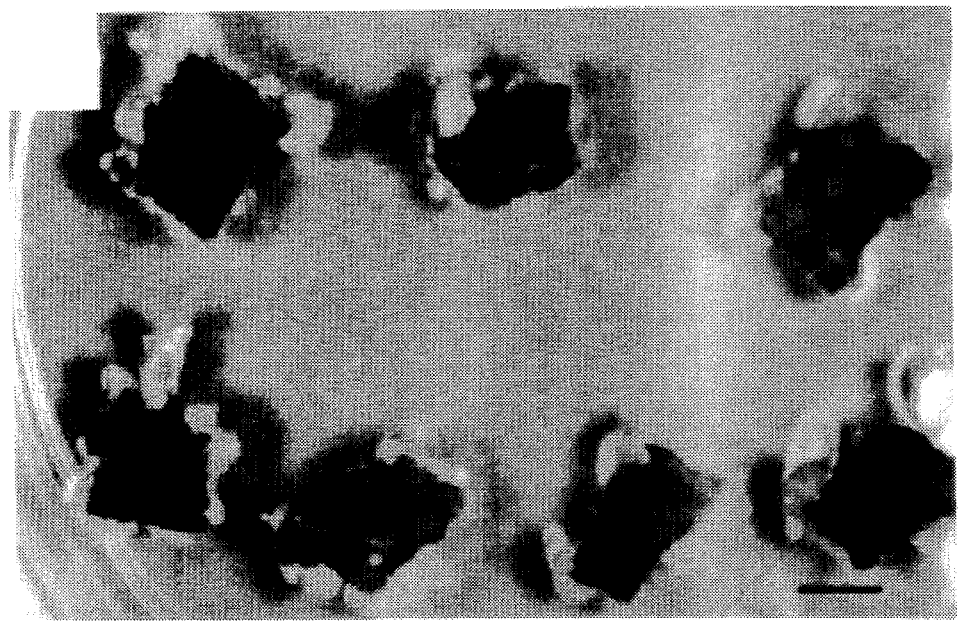
FIG. 3 shows various stages of an embryogenic cell suspension from mature leaf callus of Rosa hybrida var. Royalty. (A) Primary callus growth from mature leaf explant after 3 weeks in culture; bar 6.2 mm; (B) Compact white embryogenic tissue derived from oxidized globular callus in liquid culture; bar 1.1 mm; (C) Fine cell suspension from compact embryogenic tissue; bar 10.0 mm; (D) Regeneration of rose somatic embryos from cell suspension after 4 weeks on solid medium; bar 0.7 mm.
Figure 3B:
Figure 3C:
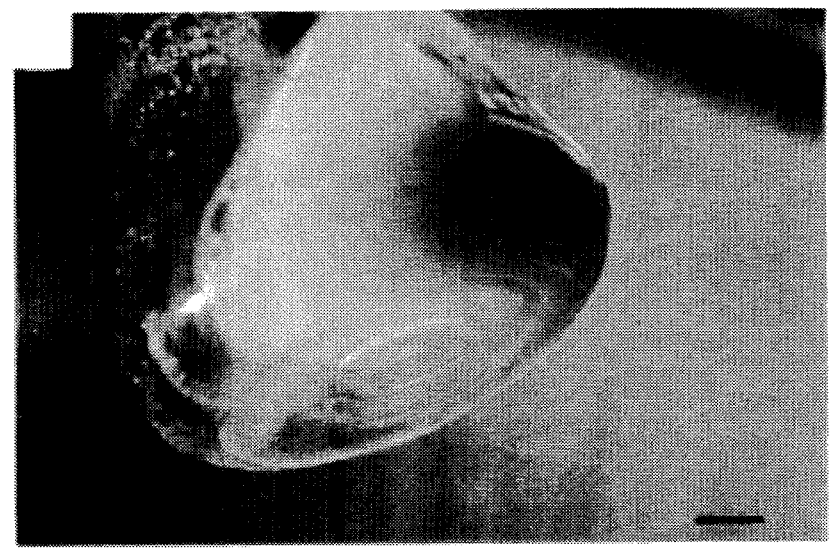
Figure 3D:
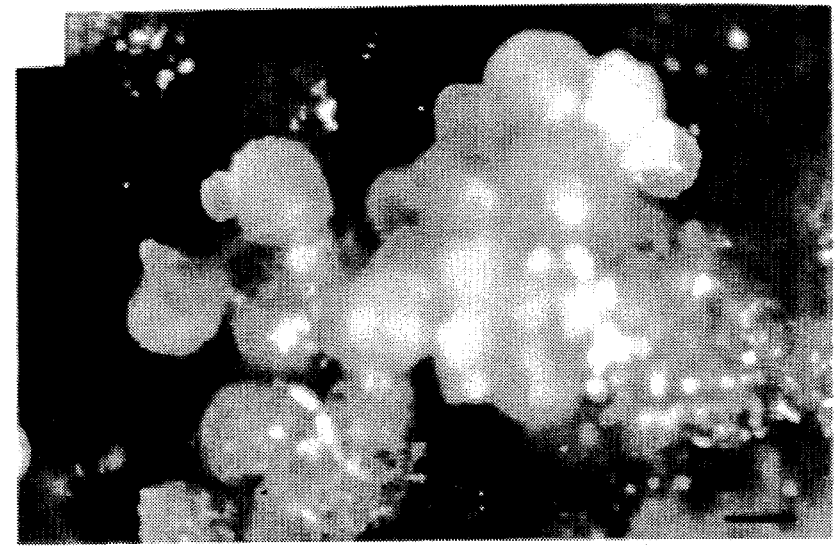

Methods used to produce somatic embryos from cell suspensions from *Rosa Hybrida* L. var. Royalty are shown in FIG. 6. Liquid cultures of *Rosa hybrida* L. var. Royalty were established from primary callus derived from mature leaves of field grown plants. Surface sterilization was accomplished with ethanol (70%) for 2 min. followed by clorox (10%)/Tween-20 (0.1%) for 8 min. Four rinses with sterile deionized water at 5 min. intervals were required. Leaf pieces of ca. 0.5 $cm^2$ were inoculated onto the following callus induction medium (M130-7): MS salts, MS vitamins supplemented with KIN (1.0 mg/l), NAA (2 mg/l), agar and maintained on a shaker at 115 rpm, under light at 24° C. Mature leaf originated hard callus 3–5 weeks after inoculation in M130-7 (FIG. 3A). Callus subcultured in liquid M130-7 oxidized after 3 weeks. This oxidation process continued during the following 10 weeks of culture in presence of a second liquid medium, M11, consisting of MS salts, thiamine-HCl (10.0 mg/l), pyridoxine (2.0 mg/l), nicotinic acid (2.0 mg/l), 2,4-D (1.0 mg/l), sucrose (30 g/l), PVP-40 (10 g/l), MES (9.9 mg/l), KM-8P vitamins, L-glutamine (5.6 mg/l), L-alanine (0.6 mg/l), L-glutamic acid (0.6 mg/l), cysteine (0.2 mg/l), and vitamin-free casaminoacids (250 mg/l); pH 5.8. In the meantime, very globular white areas arose from the deeply oxidized callus (FIG. 3B). To overcome tissue oxidation, a new liquid medium W25-3 (the same W25-1 but without agar) was utilized. No further growth was observed and tissue oxidation was complete in three weeks in this medium. A final liquid medium (SM-1; Prioli and Sondahl, 1989, *Bio/Technology* 7:589–594) was used to produce fine cell suspension from globular structures. Transference of oxidized callus into SM-1 allowed the development of a white compact embryogenic tissue, which within 3–4 weeks began to form small cell clumps. Fine cell suspensions were established from these cultures (FIG. 3C) and maintained at a density of 10 ml of packed cells/100 ml of suspension culture by a 3–4 day subculture. After two weeks in this type of liquid culture, regeneration capacity of these fine cell suspensions was evaluated on W26-1 solid medium. This regeneration medium consisted of modified White salts as in W25-1, thiamine-HCl (5 mg/l), inositol (100 mg/l), pyridoxine (1.5 mg/l), nicotinic acid (1.5 mg/l), glycine (2.0 mg/l), KIN (2.0 mg/l), NAA (0.25 mg/l), sucrose (20 g/l), and Sigma agar (6 g/l); pH 5.6. Somatic embryos at early developmental stages were visible in W26-1 after 4 weeks on regeneration medium (FIG. 3D).

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for producing a *Rosa hybrida* plantlet from a somatic embryo which comprises:
    (a) providing a somatic embryo;
    (b) culturing the somatic embryo on a maturation medium capable of inducing differentiation of the embryo to yield a differentiated embryo;
    (c) culturing the differentiated embryo on germination or regeneration medium to yield a germinated embryo, plantlet, or shoot; and
    (d) producing a mature plantlet from the germinated embryo, plantlet, or shoot.
2. The method according to claim 1 in which the maturation medium comprises effective amounts of a nutrient medium, a carbon source, and growth regulator including at least one auxin.
3. The method according to claim 2 in which the nutrient medium is selected from the group consisting of White's, B5, N6 and MS medium.
4. The method according to claim 2 in which the carbon source is a sugar.
5. The method according to claim 4 in which the sugar is selected from the group consisting of sucrose, glucose, maltose, and lactose.
6. The method according to claim 4 in which the sugar is sucrose.
7. The method according to claim 6 in which the sugar is present in the amount of about 10–50 g/l.
8. The method according to claim 2 in which abscisic acid is further present as a growth regulator.
9. The method according to claim 8 in which the abscisic acid is present at a concentration of about 0.2–2.0 mg/l.
10. The method according to claim 2 in which gibberellic acid is further present as a growth regulator.
11. The method according to claim 10 in which the gibberellic acid is present in an amount of about 0.5 mg/l to about 5.0 mg/l.
12. The method according to claim 1 in which the embryo is cultured on maturation medium for about 3–14 weeks.
13. The method according to claim 1 in which the germination medium comprises effective amounts of an N6 or MS nutrient medium and a carbon source.
14. The method according to claim 13 in which the carbon source is a sugar.
15. The method according to claim 14 in which the sugar is sucrose.
16. The method according to claim 14 in which the sugar is present in the amount of about 10–50 g/l.
17. The method according to claim 1 in which the differentiated embryo is cultured in germination medium for about 1–4 weeks.
18. The method according to claim 74 in which the propagation media comprises effective amounts of nutrient media, a carbon source, an auxin and a cytokinin.
19. The method according to claim 18 in which the nutrient medium is selected from the group consisting of White's, B5, N6 and MS medium.
20. The method according to claim 18 in which the carbon source is a sugar.
21. The method according to claim 20 in which the sugar is present in the amount of about 10–50 g/l.
22. The method according to claim 18 in which the auxin is present at a concentration of about 0.1–10 mg/l and the cytokinin is present at a concentration of about 0.2–15.0 mg/l.
23. The method according to claim 18 in which the auxin is selected from the group consisting of IAA, NAA, 2,4-D, and picloram.
24. The method according to claim 18 in which the auxin is IAA.
25. The method according to claim 18 in which the cytokinin is selected from the group consisting of 6-BA, zeatin, kinetin, and iP.
26. The method according to claim 18 in which the cytokinin is 6-BA.
27. The method according to claim 74 in which the germinated embryo is cultured in propagation medium for about 4–8 weeks.
28. A method for obtaining at least one somatic embryo from somatic cell or cells of *Rosa hybrida* which comprises:
    (a) culturing the somatic cell or cells on callus induction medium comprising effective amounts of a nutrient medium, a carbon source, an auxin and a cytokinin to obtain at least one induced callus; and
    (b) culturing the induced callus in a regeneration media comprising a nutrient media, a carbon source, an auxin and a cytokinin present in amounts effective to obtain at least one somatic embryo.
29. The method according to claim 27 in which the nutrient medium in the callus induction medium is N6 or MS medium.
30. The method according to claim 27 in which the carbon source in the callus induction medium is a sugar.

31. The method according to claim 30 in which the sugar is sucrose.

32. The method according to claim 30 in which the sugar is present in the amount of about 10–50 g/l.

33. The method according to claim 27 in which the auxin is present at a concentration of about 0.1–10 mg/l and the cytokinin is present at a concentration of about 0.2–15.0 mg/l in the callus induction medium.

34. The method of claim 27 in which the auxin in the callus induction medium is NAA.

35. The method of claim 34 in which the NAA is present at a concentration of about 0.5–2.5 mg/l.

36. The method according to claim 27 in which the cytokinin in the callus induction medium is kinetin.

37. The method according to claim 36 in which the kinetin is present at a concentration of about 0.5–5.0 mg/l.

38. The method according to claim 27 in which the cytokinin in the callus induction medium is zeatin.

39. The method according to claim 38 in which the zeatin is present at a concentration of about 0.2–12.5 mg/l.

40. The method according to claim 27 in which the callus induction medium further comprises effective amounts of abscisic acid.

41. The method according to claim 40 in which the abscisic acid is present at a concentration of about 0.1–0.2 mg/l.

42. The method according to claim 27 in which the embryo is cultured on callus induction medium for about 3–9 weeks.

43. The method according to claim 27 in which the nutrient medium in the regeneration medium is selected from the group consisting of White's, N6, MS, and B5 medium.

44. The method according to claim 27 in which the carbon source in the regeneration medium is a sugar.

45. The method of claim 27 in which the auxin in the regeneration medium is NAA.

46. The method of claim 27 in which the auxin in the regeneration medium is 2,4-D.

47. The method according to claim 27 in which the cytokinin in the regeneration medium is kinetin.

48. The method according to claim 27 in which the cytokinin in the regeneration medium is zeatin.

49. The method according to claim 27 in which the callus is cultured on regeneration medium for about 3 to 6 weeks.

50. The method according to claim 27 which further comprises after culturing the somatic tissue on callus induction medium and before culturing the induced callus in a regeneration medium, culturing the induced callus in maintenance medium to isolate the induced callus.

51. The method according to claim 50 in which the maintenance medium comprises effective amounts of a nutrient medium, a carbon source and at least one growth regulator.

52. The method according to claim 51 in which the nutrient medium is selected from the group consisting of White's, B5, N6 and MS medium.

53. The method according to claim 51 in which the carbon source is a sugar.

54. The method according to claim 51 in which the growth regulator is an auxin.

55. The method according to claim 54 in which the auxin is present at a concentration of about 0.1–10 mg/l.

56. The method according to claim 54 in which gibberellic acid is further present as a growth regulator.

57. The method according to claim 56 in which the gibberellic acid is present at a concentration of about 0.5–5.0 mg/l.

58. The method according to claim 54 in which abscisic acid is further present as a growth regulator.

59. The method according to claim 58 in which the abscisic acid is present at a concentration of about 0.2–2.0 mg/l.

60. A method for obtaining a somatic embryo from a stamen filament of *Rosa hybrida* of the cultivar Royalty which comprises:

(a) culturing the stamen filament on callus induction medium comprising effective amounts of a nutrient medium, a carbon source, and an auxin and a cytokinin to obtain at least one induced callus; and (b) culturing the induced callus in a regeneration media capable of inducing completion of the development of somatic embryos comprising effective amounts of a nutrient medium, an energy source, an auxin and a cytokinin in which the ratio of auxin to cytokinin is decreased by a factor of two to about 15 relative to the ratio of auxin to cytokinin in the callus induction medium to obtain a somatic embryo.

61. The method of claim 60 in which the source of the auxin and cytokinin in the regeneration media differs from the source of the auxin and cytokinin in the callus induction medium.

62. The method according to claim 60 which further comprises after culturing the stamen filament on callus induction medium and before culturing the callus in a regeneration medium, culturing the induced callus in maintenance medium to isolate the induced callus.

63. A *Rosa hybrida* somatic embryo.

64. A somatic embryo produced by the method of claim 28.

65. A method as in claim 1, wherein the plantlet is produced by propagating the germinated embryo or plantlet on propagation medium.

66. A method as in claim 1, wherein the plantlet is produced by transferring the germinated embryo or plantlet directly to soil.

67. A method as in claim 1, wherein multiple shoots are isolated before producing the plantlet.

68. A method as in claim 67, wherein the shoots are transferred directly to soil to produce the plantlet.

* * * * *